US008597955B2

(12) United States Patent
Skriner et al.

(10) Patent No.: US 8,597,955 B2
(45) Date of Patent: Dec. 3, 2013

(54) HNRNP A3 RELATED PEPTIDES AND USE THEREOF FOR DIAGNOSIS OF RHEUMATOID ARTHRITIS

(75) Inventors: Karl Skriner, Berlin (DE); Kerstin Adolph, Gau-Algesheim (DE); Jørg Hollidt, Berlin (DE)

(73) Assignee: Charite—Universitatsmedizin Berlin, Berlin (DE)

( * ) Notice: Subject to any disclaimer, the term of this patent is extended or adjusted under 35 U.S.C. 154(b) by 26 days.

(21) Appl. No.: 13/141,960

(22) PCT Filed: Dec. 23, 2009

(86) PCT No.: PCT/EP2009/067840
§ 371 (c)(1), (2), (4) Date: Sep. 16, 2011

(87) PCT Pub. No.: WO2010/072804
PCT Pub. Date: Jul. 1, 2010

(65) Prior Publication Data
US 2012/0070854 A1 Mar. 22, 2012

(30) Foreign Application Priority Data

Dec. 23, 2008 (EP) .................................. 08172809

(51) Int. Cl.
*G01N 33/53* (2006.01)
(52) U.S. Cl.
USPC ............................................ 436/86
(58) Field of Classification Search
None
See application file for complete search history.

(56) References Cited

U.S. PATENT DOCUMENTS

2003/0068803 A1  4/2003  Reed et al.

FOREIGN PATENT DOCUMENTS

WO     WO 98/14469     4/1998

OTHER PUBLICATIONS

Ngo et al. "Computational Complexity, Protein Structure Prediction, and the Levinthal Paradox" in the book of "The Protein Folding Problem and Tertiary Structure Prediction" editors by Merz et al. 1994).*

Well Biochem 1990 vol. 29, p. 8509-8517.*
Hayer et al., Aberrant Expression of the autoantigen Heterogeneous Nuclear Ribonucleoprotein-A2 (RA33) and Spontaneous Formation of Rheumatoid Arthritis-Associated Anti-RA33 Autoantibodies in TNF-α Transgenic Mice, *Journal of Immunology*, vol. 175, No. 12, (2005) XP-002518173.
Siapka et al., Multiple specificities of autoantibodies against hnRNP A/B proteins in systemic rheumatic disease and hnRNP L as an associated novel autoantigen, *Autoimmunity*, vol. 40, No. 3, (2007) XP-009113371.
E. Suleymanoglu, Circular dichroism and fluorescence spectroscopic study of RNA-protein folding patterns in human hnRNP A3 and their implications in human autoimmune diseases, *Prog. Biochem. Biophys.*,vol. 31, No. 3, pp. 219-224 (2004) XP-002518174.
Steiner et al., Novel autoantibodies for the diagnosis of rheumatoid arthritis, *Zeitschrift Für Rheumatologie*, vol. 61, No. 6 (2002) XP-002518175.
Simone et al., The cytokeratin filament-aggregating protein filaggrin is the target of the so-called "Antikeratin Antibodies," autoantibodies specific for rheumatoid arthritis, *J. Clin. Invest.*, vol. 92, 1387-1393 (1993).
Young et al., Anti-keratin antibodies in rheumatoid arthritis, *British Medical Journal*, vol. 2, 97-99 (1979).
Gregorius et al., Hydrocoating: a new method for coupling biomolecules to solid phase, *Journal of Immunological Methods*, 181 (1995) p. 65-73.
Vincent et al., High diagnostic value in rheumatoid arthritis of antibodies to the stratum corneum of rat oesophagus epithelium, so-called antikeratin antibodies, *Annals of the Rheumatic Diseases*, vol. 48, pp. 712-722 (1989).
Paimela et al., Antikeratin antibodies: diagnostic and prognostic markers for early rheumatoid arthritis, *Annals of the Rheumatic Diseases*, vol. 51, pp. 743-746 (1992).
Chorev et al., Recent developments in retro peptides and proteins-an ongoing topochemical exploration, *Elsevier Science Ltd.*, vol. 13, (1995).
Young et al., Anti-keratin antibodies in rheumatoid arthritis, *British Medical Journal*, vol. 2, p. 97-99 (1979).
Simon et al., The cytokeratin filament-agreegating protein filaggrin is the target of the so-called "Antikeratin Antibodies," Auto specific for rheumatoid arthritis, *J. Clin. Invest.*, vol. 92, p. 1387-1393 (1993).
Vincent et al., natural IgG to the stratum corneum of the rat oesophagus epithelium, so-called 'antikeratin antibodies', in rheumatoid arthritis and other rheumatic diseases, *Journal of Autoimmunity*, vol. 4, issue 3, (1991).

* cited by examiner

*Primary Examiner* — Jacob Cheu
(74) *Attorney, Agent, or Firm* — Enshan Hong; Kent H. Cheng; VLP Law Group LLP

(57) ABSTRACT

The invention relates to a peptide and retro or retro-inverso peptide thereof, with a length of ≤25 amino acid residues, characterized in that the peptide comprises at least one citrulline residue, and exhibits a sequence identity over the whole sequence of the peptide of ≥70% compared to human hnRNP A3 protein (SEQ ID No. 1) and uses thereof.

10 Claims, 1 Drawing Sheet

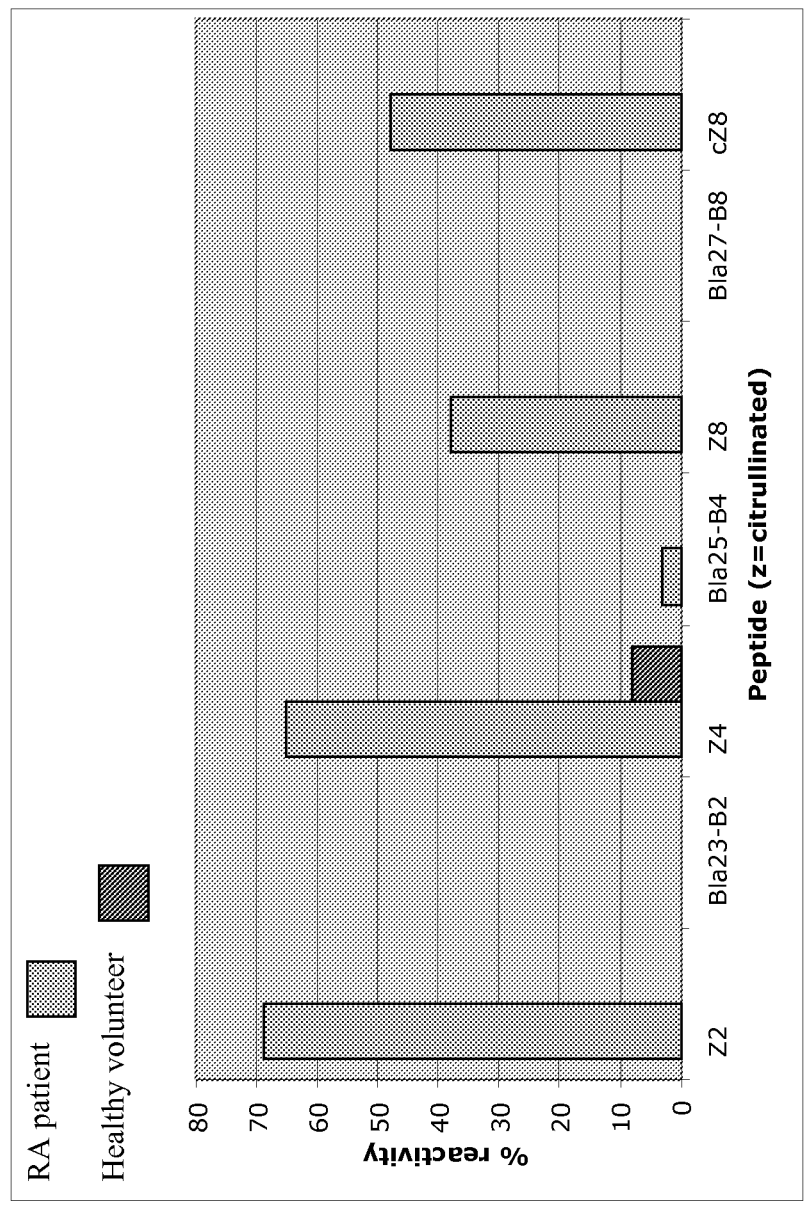

SEQUENCE LISTING

```
<160> NUMBER OF SEQ ID NOS: 29

<210> SEQ ID NO 1
<211> LENGTH: 378
<212> TYPE: PRT
<213> ORGANISM: Homo sapiens

<400> SEQUENCE: 1

Met Glu Val Lys Pro Pro Gly Arg Pro Gln Pro Asp Ser Gly Arg
1               5                   10                  15

Arg Arg Arg Arg Gly Glu Glu Gly His Asp Pro Lys Glu Pro Glu
            20                  25                  30

Gln Leu Arg Lys Leu Phe Ile Gly Gly Leu Ser Phe Glu Thr Thr Asp
            35                  40                  45

Asp Ser Leu Arg Glu His Phe Glu Lys Trp Gly Thr Leu Thr Asp Cys
        50                  55                  60
```

```
Val Val Met Arg Asp Pro Gln Thr Lys Arg Ser Arg Gly Phe Gly Phe
 65                  70                  75                  80

Val Thr Tyr Ser Cys Val Glu Val Asp Ala Ala Met Cys Ala Arg
                 85                  90                  95

Pro His Lys Val Asp Gly Arg Val Glu Pro Lys Arg Ala Val Ser
            100                 105                 110

Arg Glu Asp Ser Val Lys Pro Gly Ala His Leu Thr Val Lys Lys Ile
            115                 120                 125

Phe Val Gly Gly Ile Lys Glu Asp Thr Glu Glu Tyr Asn Leu Arg Asp
            130                 135                 140

Tyr Phe Glu Lys Tyr Gly Lys Ile Glu Thr Ile Glu Val Met Glu Asp
145                 150                 155                 160

Arg Gln Ser Gly Lys Lys Arg Gly Phe Ala Phe Val Thr Phe Asp Asp
                165                 170                 175

His Asp Thr Val Asp Lys Ile Val Val Gln Lys Tyr His Thr Ile Asn
                180                 185                 190

Gly His Asn Cys Glu Val Lys Lys Ala Leu Ser Lys Gln Glu Met Gln
            195                 200                 205

Ser Ala Gly Ser Gln Arg Gly Arg Gly Gly Ser Gly Asn Phe Met
    210                 215                 220

Gly Arg Gly Gly Asn Phe Gly Gly Gly Gly Asn Phe Gly Arg Gly
225                 230                 235                 240

Gly Asn Phe Gly Gly Arg Gly Gly Tyr Gly Gly Gly Gly Gly Ser
                245                 250                 255

Arg Gly Ser Tyr Gly Gly Gly Asp Gly Gly Tyr Asn Gly Phe Gly Gly
                260                 265                 270

Asp Gly Gly Asn Tyr Gly Gly Gly Pro Gly Tyr Ser Ser Arg Gly Gly
                275                 280                 285

Tyr Gly Gly Gly Pro Gly Tyr Gly Asn Gln Gly Gly Gly Tyr Gly
    290                 295                 300

Gly Gly Gly Gly Tyr Asp Gly Tyr Asn Glu Gly Gly Asn Phe Gly Gly
305                 310                 315                 320

Gly Asn Tyr Gly Gly Gly Asn Tyr Asn Asp Phe Gly Asn Tyr Ser
                325                 330                 335

Gly Gln Gln Gln Ser Asn Tyr Gly Pro Met Lys Gly Gly Ser Phe Gly
                340                 345                 350

Gly Arg Ser Ser Gly Ser Pro Tyr Gly Gly Gly Tyr Gly Ser Gly Gly
            355                 360                 365

Gly Ser Gly Gly Tyr Gly Ser Arg Arg Phe
            370                 375

<210> SEQ ID NO 2
<211> LENGTH: 59
<212> TYPE: PRT
<213> ORGANISM: Homo sapiens

<400> SEQUENCE: 2

Gly Gly Asn Phe Gly Gly Gly Gly Asn Phe Gly Arg Gly Gly Asn
 1               5                  10                  15

Phe Gly Gly Arg Gly Gly Tyr Gly Gly Gly Gly Gly Ser Arg Gly
                20                  25                  30

Ser Tyr Gly Gly Gly Asp Gly Gly Tyr Asn Gly Phe Gly Asp Gly
            35                  40                  45

Gly Asn Tyr Gly Gly Gly Pro Gly Tyr Ser Ser
    50                  55
```

```
<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Citrulline

<400> SEQUENCE: 3

Gly Gly Gly Gly Gly Asn Phe Gly Xaa Gly Gly Asn Phe Gly Gly
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Gly Asn Phe Gly Arg Gly Gly Asn Phe Gly Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Citrulline

<400> SEQUENCE: 5

Gly Tyr Gly Gly Gly Gly Gly Gly Ser Xaa Gly Ser Tyr Gly Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Gly Gly Gly Gly Gly Gly Ser Arg Gly Ser Tyr Gly Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (11)..(11)
```

```
<223> OTHER INFORMATION: Citrulline

<400> SEQUENCE: 7

Asn Phe Gly Xaa Asp Gly Asn Phe Gly Gly Xaa Gly Gly Tyr Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Phe Gly Arg Asp Gly Asn Phe Gly Gly Arg Gly Gly Tyr Gly
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 9

Cys Asn Phe Gly Xaa Asp Gly Asn Phe Gly Gly Xaa Gly Gly Tyr Gly
1               5                   10                  15

Cys

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Citrulline

<400> SEQUENCE: 10

Gly Gly Phe Asn Gly Gly Xaa Gly Phe Asn Gly Gly Gly Gly Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Citrulline

<400> SEQUENCE: 11

Gly Gly Tyr Ser Gly Xaa Ser Gly Gly Gly Gly Gly Gly Tyr Gly
1               5                   10                  15
```

```
<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 12

Gly Tyr Gly Gly Xaa Gly Gly Phe Asn Gly Asp Xaa Gly Phe Asn
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Citrulline
<220> FEATURE:
<221> NAME/KEY: MOD_RES
<222> LOCATION: (13)..(13)
<223> OTHER INFORMATION: Citrulline

<400> SEQUENCE: 13

Cys Gly Tyr Gly Gly Xaa Gly Gly Phe Asn Gly Asp Xaa Gly Phe Asn
1               5                   10                  15

Cys

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Citrulline

<400> SEQUENCE: 14

Gly Asn Phe Met Gly Xaa Gly Gly Asn Phe Gly Gly Gly Gly Gly
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Citrulline

<400> SEQUENCE: 15
```

```
Gly Asn Phe Gly Gly Xaa Gly Gly Tyr Gly Gly Gly Gly Gly
1               5                  10                  15
```

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Citrulline

<400> SEQUENCE: 16

```
Gly Gly Gly Gly Gly Phe Asn Gly Gly Xaa Gly Met Phe Asn Gly
1               5                  10                  15
```

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Citrulline

<400> SEQUENCE: 17

```
Gly Gly Gly Gly Gly Gly Tyr Gly Gly Xaa Gly Gly Phe Asn Gly
1               5                  10                  15
```

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (8)..(8)
<223> OTHER INFORMATION: Citrulline

<400> SEQUENCE: 18

```
Cys Asp Ser Gly Xaa Arg Arg Xaa His Trp Gly Glu Glu Gly His Cys
1               5                  10                  15
```

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Citrulline
<220> FEATURE:
<221> NAME/KEY: MOD_RES
<222> LOCATION: (8)..(8)
<223> OTHER INFORMATION: Citrulline

<400> SEQUENCE: 19

Ser Ala Gly Ser Xaa Xaa Gly Xaa Gly Gly Ser Gly Asn Phe
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (14)..(14)
<223> OTHER INFORMATION: Citrulline

<400> SEQUENCE: 20

Gly Tyr Asn Xaa Phe Gly Gly Asp Gly Gly Asn Tyr Gly Xaa Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 21

Gly Gly Tyr Asn Xaa Phe Gly Gly Asp Gly Gly Xaa Tyr Gly Ser
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Citrulline
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (14)..(14)
<223> OTHER INFORMATION: Citrulline

<400> SEQUENCE: 22

Ser Xaa Gly Ser Tyr Gly Gly Gly Xaa Gly Gly Tyr Asn Xaa Phe
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
        peptide
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 23

Ala Met Xaa Ala Xaa Pro Phe Lys Val Asp Gly Xaa Val Val Glu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 24

Cys His Gly Glu Glu Gly Trp His Xaa Arg Arg Xaa Gly Ser Asp Cys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (8)..(8)
<223> OTHER INFORMATION: Citrulline
<220> FEATURE:
<221> NAME/KEY: MOD_RES
<222> LOCATION: (10)..(11)
<223> OTHER INFORMATION: Citrulline

<400> SEQUENCE: 25

Phe Asn Gly Ser Gly Gly Gly Xaa Gly Xaa Xaa Ser Gly Ala Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (2)..(2)
<223> OTHER INFORMATION: Citrulline
<220> FEATURE:
<221> NAME/KEY: MOD_RES
<222> LOCATION: (12)..(12)
<223> OTHER INFORMATION: Citrulline
```

-continued

```
<400> SEQUENCE: 26

Ser Xaa Gly Tyr Asn Gly Gly Asp Gly Gly Phe Xaa Asn Tyr Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (11)..(11)
<223> OTHER INFORMATION: Citrulline

<400> SEQUENCE: 27

Ser Gly Tyr Xaa Gly Gly Asp Gly Gly Phe Xaa Asn Tyr Gly Gly
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Citrulline
<220> FEATURE:
<221> NAME/KEY: MOD_RES
<222> LOCATION: (7)..(7)
<223> OTHER INFORMATION: Citrulline
<220> FEATURE:
<221> NAME/KEY: MOD_RES
<222> LOCATION: (14)..(14)
<223> OTHER INFORMATION: Citrulline

<400> SEQUENCE: 28

Phe Xaa Asn Tyr Gly Gly Xaa Gly Gly Gly Tyr Ser Gly Xaa Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (11)..(11)
<223> OTHER INFORMATION: Citrulline
<220> FEATURE:
<221> NAME/KEY: MOD_RES
<222> LOCATION: (13)..(13)
<223> OTHER INFORMATION: Citrulline

<400> SEQUENCE: 29

Glu Val Val Xaa Gly Asp Val Lys Phe Pro Xaa Ala Xaa Met Ala
1               5                   10                  15
```

HNRNP A3 RELATED PEPTIDES AND USE THEREOF FOR DIAGNOSIS OF RHEUMATOID ARTHRITIS

PRIORITY CLAIM

This is a U.S. national stage of application No. PCT/EP2009/067840, filed on Dec. 23, 2009. Priority is claimed on the following application: EP Application No.: 08172809.9 Filed on Dec. 23, 2008, the content of which is incorporated here by reference.

SEQUENCE LISTING

The instant application contains a Sequence Listing which has been submitted in ASCII format via EFS-Web and is hereby incorporated by reference in its entirety. Said ASCII copy, created on Nov. 18, 2011, is named 566119US.txt and is 14,361 bytes in size.

TECHNICAL FIELD OF THE INVENTION

This invention relates to new hnRNP A3 related peptides reacting with rheumatism-associated autoantibodies, the use of these peptides and a diagnostic kit comprising said peptides. Furthermore, this invention is directed to a method of detecting autoantibodies against said peptides.

BACKGROUND OF THE INVENTION

Rheumatic diseases are among the most common diseases in Germany. A diagnostic test which allows to attribute the medical condition of a particular patient to harmless muscle tenseness, arthrosis or to the most frequent and severe of said diseases, rheumatoid arthritis (RA) is not known to date.

Rheumatoid arthritis is an autoimmune disease in which the defence mechanisms of the human body erroneously regard endogenous joint cartilage as foreign and hostile and attack said cartilage. Approximately 1 out of 100 humans in western European countries suffers from rheumatoid arthritis. The disease progresses very rapidly in the first few months.

An important key strategy in modern rheumatology is therefore the early onset of treatment e.g. with drugs which may positively modify the course of the disease. Numerous clinical studies have shown that very good therapeutic success and response rates can be achieved using suitable active compounds, for example TNF antagonists, if said compounds are used in patients already in the early stages of the disease. Rheumatologists try to utilize the narrow time window between the onset of the disease and the occurrence of structural joint damage. To date, however, no reliable and sensitive detection of rheumatoid arthritis within said time window has been disclosed in the prior art.

Rheumatoid arthritis is diagnosed according to the classification criteria of the ACR (American College of Rheumatology). According to the criteria of the ACR, the rheumatoid factor is currently the fundamental serological indicator for diagnosing rheumatoid arthritis (RA). Rheumatoid factors are a subgroup of immunoglobulins which are distinguished by immunological cross reaction to the Fc region of immunoglobulin G (IgG). However, the presence of a rheumatoid factor is not limited to disorders of the rheumatic type (therefore necessitating a differential-diagnostic evidence), and rheumatoid factors are also found in the serum of patients suffering from infectious diseases, hyperglobulinemias, lymphoproliferative B cell disorders, and generally in the older population.

Usually, elevated concentrations of rheumatoid factors are associated with a more severe course of the disease. Said concentrations do not correlate with the degree of activity and the therapeutic success. A sensitive and specific prognosis of the onset of rheumatoid arthritis cannot be made on the basis of the concentration of rheumatoid factors. Healthy persons may have an elevated rheumatoid factor concentration without being affected, while some patients without elevated rheumatoid factor concentrations suffer from a very aggressive form of rheumatoid arthritis.

Other serological markers such as anti-citrulline antibody (CCP) or the initial HAQ score which is used to assess abilities in daily life or X-ray or computer tomography (CT) imaging provide only little information on the early form and are, by themselves, not meaningful enough in order to be able to assess the prognosis of the patient.

In order to optimise the existing classification criteria of the ACR, the American College of Rheumatology proposes seven classification criteria which indicate a poor prognosis:
1. morning stiffness of the joints lasting more than one hour,
2. arthritis of three or more joints,
3. inflammation of at least three joint areas at the same time,
4. hand joints or finger joints are likewise affected,
5. bilateral tenderness of metacarpophalangeal joints to pressure,
6. erosions on radiographs, and
7. detection of special rheumatoid factors and anti-perinuclear factor positivity (APF).

Autoantibodies to the "anti-perinuclear factor" were first described by Young et al. for patients having rheumatoid arthritis (Young, B. J. J. et al., Antikeratin antibodies in rheumatoid arthritis, B.M.J., 2 (1979), 97-99). Owing to their specific reaction to the keratinous epithelium of the stratum corneum on rat oesophagus sections, keratin has long been considered to be the corresponding antigen (Vincent, C. H. et al.; High diagnostic value in rheumatoid arthritis of antibodies to the stratum corneum of rat oesophagus epithelium, so-called "antikeratin antibodies", Ann. Rheumat. Dis. 48 (1989), 712-722). For this reason, the antibodies are even today referred to as antikeratin antibodies (AKAs) (Vincent, C. H. et al, Natural IgG to Epidermal Cytokeratins vs IgG to the Stratum Corneum of the Rat Oesophagus Epithelium, so-called "Antikeratin Antibodies", in Rheumatoid Arthritis and other Rheumatic Diseases; J. of Autoimmunity 4 (1991), 493-505; F'aimela, L. et al., Antikeratin antibodies: diagnostic and prognostic markers for early rheumatoid Arthritis, Ann. Rheumat. Dis., 51 (1992) 743-746).

Later studies have demonstrated that at least some AKA or APF reactive sera also exhibit anti-filaggrin antibody activity. Thus the basic protein filaggrin has been identified as a target antigen. The 40 kDa protein aggregates cytokeratin filaments and assists in forming the intracellular fiber matrix of the keratinous cells (Simon, M. et al., The Cytokeratin Filament-Aggregating Protein Filaggrin is the Target of the So-called "Antikeratin Antibodies", Autoantibodies Specific for Rheumatoid Arthritis, J. Clin. Invest., 92 (1993), 1387-93).

Since sera containing APFs, AKAs and anti-filaggrin antibodies react in the same way, these antibody systems appear to be identical. Anti-filaggrin antibodies of the IgG type which have a specificity of more than 99% are a highly specific marker for rheumatoid arthritis. Several studies found positive correlations with respect to severity and activity of the disease. Anti-filaggrin antibodies do not correlate with age, sex or duration of the disease.

Using currently customary methods, however, said antibodies can be found in the serum of only approx. 40% of RA cases.

It was therefore the object of the present invention to provide novel polypeptides for detecting antibodies associated with rheumatoid arthritis, that allow for an improved diagnosis of RA.

SOLUTION PROVIDED BY THE INVENTION

This problem was solved by the present invention by providing a peptide and the retro or retro-inverso peptide thereof, with a length of 25 amino acid residues, characterized in that the peptide
- a) comprises at least one citrulline residue, and
- b) exhibits a sequence identity over the whole sequence of the peptide of 70% compared to human hnRNP A3 protein (SEQ ID No. 1).

It was surprisingly found that such peptides of the invention were detected by autoantibodies from body fluids of a remarkable number of RA patients, while virtually no specific reactivity was found with body fluids of individuals with non-RA rheumatic disease, osteoarthritis or of healthy volunteers (see Table 1). Furthermore, the peptides of the invention reveal specific reactivity with body fluids of RA patients that have been negative in anti-CCP ELISA (see Table 2). In a comparison of an ELISA of peptides of the invention and anti-CCP ELISA, RA was predicted with improved sensitivity and specificity over anti-CCP ELISA alone (see Table 3). Surprisingly, the peptides of the invention turned out to be particularly useful in diagnosis of RA with an erosive course of disease (see Table 3). Thus, use of the peptides of the present invention allows an improved diagnosis of RA and further contributes to a diagnosis of RA without the need of a differential diagnosis scheme.

The peptide of the present invention is a polymer formed by linking amino acid residues to each other via a peptide bond. Peptides according to the invention may be formed from α-, β-, and γ-, and/or D- and L-amino acids. The peptides may comprise naturally occurring amino acids, modified natural amino acids and/or synthetic amino acids. The peptides of the invention may comprise amino acids that carry one or more modifications at their side-groups, amino terminus and/or carboxy terminus. Said peptides may be modified in order to exhibit desired functional groups, like e.g. an alkyl radical, a carboxylic acid group, an amino group and/or an ester group. Said peptide may also be a cyclic peptide. The skilled person is aware of suitable techniques to manufacture cyclic peptides or otherwise modified peptides.

The invention is also directed to the retro-variant of the peptide of the invention. The retro-peptide according to the invention is produced by reversing the sequence of the peptide of the invention and making the C-terminal amino acid into the N-terminal amino acid. By doing so, a retro-peptide, i.e. the mirror image peptide of the peptide of the invention is formed. This retro-peptide can be expected to have similar physico-chemical properties and surface structure as the antero-peptide.

The invention is also directed to the retro-inverso peptide of the peptide of the invention. Retro-inverso peptides are isomers of linear peptides in which the direction of the sequence is reversed (retro) and the chirality, D or L, of each amino acid is inverted (inverso). The term retro-inverso peptide is to be understood to encompass also partially modified retro-inverso isomers of the peptide of the invention in which only some of the peptide bonds are reversed and the chirality of the amino acid residues in the reversed portion is inverted.

The major advantage of such retro-inverso peptides is their enhanced activity in vivo or during contact with isolated body fluids due to improved resistance to proteolytic degradation (For review, see Chorev et al., Trends Biotech., 13:438 445, 1995).

The peptide of the invention has a length of 25 amino acid residues. In a preferred embodiment, the length of the peptide is selected from 20 to 5 amino acids, more preferably from 16 to 10 amino acids, most preferred the peptide has a length of 15 amino acid residues.

The peptide of the invention comprises at least one citrulline amino acid residue. The peptide may comprise more than one citrulline residue. The citrulline residue may be located at the C-terminus, the N-terminus or at any position in-between the N- and C-terminus of the sequence of the peptide of the invention. In a preferred embodiment of the invention, the at least one citrulline residue is located at a position in the sequence of the peptide of the invention corresponding to an arginine residue in the respective sequence of human hnRNP A3 protein.

The peptide of the invention exhibits a sequence identity over the whole sequence of the peptide of ≥70% compared to human hnRNP A3 protein (SEQ ID No. 1; SWISS PROT ID No. P51991). Preferably the peptide of the invention exhibits a sequence identity over the whole sequence of the peptide of ≥80% compared to human hnRNP A3 protein (SEQ ID No. 1), more preferably of ≥90%, most preferably of 95%. The sequence identity can be determined by using the blastp algorithm (available via http://blast.ncbi.nlm.nih.gov/Blast.cgi). In case the sequence identity between hnRNP A3 and a retro or retro-inverso peptide is to be determined, the actual sequence comparison is conducted with the antero-peptide sequence of the corresponding peptide of the invention.

The peptide of the invention can encompass one or more amino acids which differ from the corresponding sequence motif of SEQ ID No. 1. One or more of the following amino acid differences can be present in preferred peptides of the invention: 20 (R>H), 21(R>W), 64(V>L), 98(E>T), 176 (C>R), 240 (G>D), 279(G>S), 283(Y<C), 359 (G<S); wherein the numbers give the respective amino acid position within SEQ ID No. 1.

In a preferred embodiment, the peptide of the invention exhibits a sequence identity over the whole sequence of the peptide of ≥70%, preferably ≥80%, more preferably ≥90%, most preferably ≥95%, compared to a sequence selected from amino acids No 227 (G) to 285 (S) of hnRNP A3, which is designated SEQ ID No. 2.

In a further preferred embodiment, the peptide of the invention has the sequence of one of the sequences with the SEQ ID No. 3, 5, 7, or 9 to 29.

In another preferred embodiment, the peptide of the invention has the sequence of SEQ ID No. 3, SEQ ID No. 5, SEQ ID No. 7, or SEQ ID No. 9 and the retro peptides thereof with the SEQ ID No. 10, SEQ ID No. 11, SEQ ID No. 12 and SEQ ID No. 13, respectively, wherein the peptides with SEQ ID No. 9 and SEQ ID No. 13 are cyclic peptides.

The peptide of the invention may further comprise an effector entity covalently coupled to the peptide via a linker structure. An effector entity in the sense of the present invention can be any molecule that allows for or facilitates a specific use of the peptide. Preferred effector entities e.g. allow for:
  immobilisation of the peptide to a carrier, like e.g. a polymeric compound, preferably a polystyrene or polystyrole molecule, a bead, a magnetic bead, microspheres compatible with the xMAP® technology of Luminex Corporation or the like, a tag, preferably a His-tag, biotin, streptavidin, Ahx-biotin etc.;

detection of the peptide in vitro and/or in vivo, like a bead or microsphere compatible with the xMAP® technology of Luminex Corporation, a fluorescent dye, a radioactive dye, a dye compatible with another dye to give a FRET pair of dyes, a dye compatible with CT or MR detection, or any other detectable dye; and/or purification of the peptide, like e.g. a tag, preferably a His-tag, biotin, streptavidin, BSA, Ahx-biotin etc.

The effector is covalently coupled to the peptide of the invention via a linker structure. Said linker structure can be a covalent bond or any molecule suitable to connect the effector to the peptide without substantially diminishing the functionality of the effector and the peptide. In a preferred embodiment the linker is a biotin aminohexanoic acid (Ahx-biotin) coupled to the C- and/or the N-terminus of the peptide of the invention.

The invention further relates to a nucleic acid encoding a peptide of the invention. Examples of suitable nucleic acids are DNA and RNA, in particular cDNA. Said nucleic acids may be cloned into customary eukaryotic or prokaryotic vectors and expressed in suitable host cells for recombinant preparation of the peptide of the invention.

In a further aspect, the invention relates to a kit for diagnosing a disease comprising a peptide according to the invention. In a preferred embodiment the kit is used for diagnosis of rheumatoid arthritis. The kit may comprise a peptide of the invention with a single specific sequence. Alternatively, the kit can further comprise a second or more peptides according to the invention. Furthermore, the kit can further comprise CCP and/or a MCV peptide as defined in WO 07/000320.

In addition, the diagnostic kit may comprise customary components such as buffers, solvents, a suitable carrier and/or labelling groups. Suitable carriers are macromolecules such as DNA, RNA, medically compatible polymers such as, for example, polyethylene, poly-D,L-lactides, poly-D,L-lactide coglycolides, synthetic biopolymers such as, for example, polylysines and dextrans, and proteins such as, for example, serum albumin and hemocyanine. Preference is given to using dextrans in a "hydrocoating coating process" (Gregorius, K., Mouritsen, S. and Elsner, H. I., Hydrocoating: a new method for coupling biomolecules to solid phases, J. Immunol. Methods 12 (1995), 65-73).

According to another aspect of the invention, the peptide of the invention can be used for diagnosing rheumatoid arthritis, preferably for diagnosing early rheumatoid arthritis. The peptide of the invention can also be used to distinguish an erosive course of disease from a non-erosive course. In an embodiment of the invention, the peptide of the invention is used for manufacturing a medicament for diagnosing rheumatoid arthritis.

In another aspect of the invention, a method is provided for in vitro detection of antibodies against a peptide of the invention comprising the steps:
a) use of an isolated body fluid and a peptide according the invention,
b) bringing in contact isolated body fluid and the peptide of step a), and
c) determine, whether antibodies from isolated body fluid are bound to the peptide.

Said Method permits determining the presence and/or the concentration of autoantibodies against the peptide of the invention in a given body fluid and allows for a diagnosis to be made and classification and/or evaluation of the severity of the disease.

In the method according to the invention isolated body fluid is used. Preferred body fluids are blood, plasma, serum, synovial fluid, urine, feces, interstital fluid, lymphatic fluid, saliva, sudor, spinal fluid, and/or lacrimal fluid, particularly preferred are blood, plasma, serum, lymphatic fluid and/or synovial fluid.

In the method according to the invention, the isolated body fluid is contacted with at least one peptide of the invention. In another embodiment of the method, the isolated body fluid is contacted with a second or more peptides of the invention. In a preferred embodiment of the method, the isolated body fluid is contacted additionally to CCP and/or a MCV peptide as defined in WO 07/000320. In the method of the invention, binding of antibodies from the isolated body fluid to two or more of the multiple components named above is determined simultaneously in one sample in form of a multiplex assay system.

Detection methods which may be used in the method of the invention comprise any method customary in the field of diagnostics, such as e.g.
a) enzymological methods,
b) methods based an luminescence, or
c) radiochemical methods.

Preferred suitable detection methods in the process of the invention are a radioimmunoassay (RIA), a chemoluminescence immunoassay, an immunoblot assay (e.g. western blot based assays) or an enzyme immunoassay, for example an ELISA, or a lateral flow assay or a test strip assay.

According to one embodiment of the method of the invention, the body fluid to be analyzed is contacted to a peptide of the invention bound to a carrier. After incubation of said sample, unbound components are washed off. The autoantibodies specifically bound to the peptide of the invention are detected by means of a secondary binder carrying a detectable moiety. The detectable moiety can be any moiety that can be coupled to a given secondary binder and that allows for detection of the presence of said moiety. Examples of detectable moieties suitable for the method of the invention comprise an enzyme such as, for example, peroxidase or alkaline phosphatase, a radiolabel or a luminescent labeling group such as, for example, acridinium compounds.

As secondary binder, any compound can be used that allows for specific binding of the secondary binder to antibodies from the body fluid specifically bound to a peptide of the invention. The secondary binder may bind directly to the antibody from the body fluid or may e.g. be specific for the complex formed of the antibody from the body fluid bound to the peptide of the invention. Examples of suitable secondary binders suitable for the method of the invention are antibodies, fragments or derivatives thereof, peptides, nucleic acids or combinations thereof directed to and specific for human antibodies such as, for example, IgG, IgM, IgA or/and IgE, for example the Fc portion of human IgG.

In accordance with the method of the invention, binding of an antibody from the body fluid to the peptide of the invention can be determined either by increase in detectable signal. In this assay format, a secondary binder is used, which binds to antibody from the body fluid bound to the peptide of the invention directly or to a complex formed of an antibody bound to peptide or that detects a conformational change in the peptide of the invention upon occurrence of binding between antibody from body fluid and peptide of the invention.

Alternatively in a method of the invention, binding of an antibody from the body fluid to the peptide o the invention can be determined by detecting a decrease in signal. In this assay format, a secondary binder is used, that binds directly to the peptide of the invention and competes with an antibody from the body fluid for the same epitope of the peptide. If the test sample contains antibody specific for the peptide of the invention, said antibody competes with the secondary binder for binding to the peptide. An equilibrium is reached and depending on the amount of specific antibody from the body fluid present in the sample, a more or less pronounced decrease in signal is detectable.

The present invention is illustrated by the following figures and examples.

FIGURES

FIG. 1 Reactivity of peptides of the invention with serum of RA patients and healthy volunteers compared to non-Citrullinated counterparts.

EXAMPLES

Example 1

NeutrAvidin-Peptide-Antibody-ELISA

For the detection of antibodies against the peptides of the invention, a non-competitive single-site immunoassay was used with NeutrAvidin™-coated microtiter plates (Pierce, Rockford USA). The peptide was synthesized, biotinylated and lyophilized (Biotin-Ahx-HSXXXXXXXXXXXX(-CONH2). First, a stock of peptide was produced in distilled water (concentration: 1 mg/mL).

1 µL of this solution is enough for coating one well (corresponds approximately 500 pmoL peptide per well) in a total volume of 120 µL Protein-Free Blocking Buffer (Pierce, Rockford USA). The coated plates were shaken for 1 hour at room temperature (600 rpm) and incubated overnight at 4° C. The following work steps of the test procedure are listed in Table below (all steps at room temperature).

| work step | buffer/material | volume per well | incubation/ conditions |
| --- | --- | --- | --- |
| wash | PBS + 0.1% Tween20 | 300 µL | once for 1 min, 600 rpm |
| block | PBS + 5% milk powder | 140 µL | 1 Stunde, 600 rpm |
| wash | PBS + 0.1% Tween20 | 300 µL | 3-times, each case 1 min, 600 rpm |
| incubation with primary antibody | dilute sera 1:200 in PBS + 5% milk powder | 120 µL | 1 hour, 450 rpm |
| wash | PBS + 0.1% Tween20 | 300 µL | 3-times, each case 1 min, 600 rpm |
| incubation with secondary antibody | dilute the enzyme-labeled antibody-cojugate in PBS + 5% milk powder (α-human IgG-HRP, 1:5000) | 120 µL | 30 min, 600 rpm |
| wash | PBS + 0.1% Tween20 | 300 µL | 4-times, each case 1 min, 600 rpm |
| development of the colour | TMB Substrat (BlauFast) | 100 µL | wait 5 minutes |
| stop the development | 0.5M sulphuric acid | 100 µL | — |
| measurement at 450 nm | ELISA-Reader | — | — |

(Ref: 620 nm)

Here is a scheme of the plate. The black wells are coated with peptide in Protein-Free-Blocking-Buffer and the white wells are the serum controls. For each serum in double-determination you need four wells (black frame).

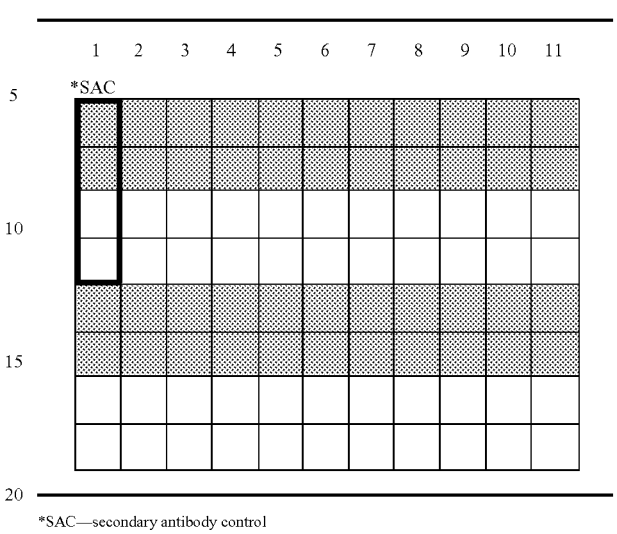

*SAC—secondary antibody control

With the raw OD values of each sample (serum and the belonging serum control) in each case the median value is generated. By subtracting SAC and Blank the net values are obtained. Then the difference of the two net values is calculated.

From the statistical analysis of healthy controls, the Peptide-specific Cut-off value is derived. For the positive/negative-evaluation, the double Cut-off level is used to reduce false positive sera (high specificity).

Example 2

Purpose of this experiment was to elucidate whether peptides of the invention can be used to diagnose specifically RA.

Sera (see table) from patients with RA, SLE, MCTD, systemic sclerosis, poly/dermatomyositis, primary Sjögren's syndrome, reactive arthritis, and osteoarthritis and healthy controls were investigated. The sera were taken from the local serum bank of and were derived from clinically and serologically well-defined patients. All RA patients fulfilled the 1987 revised criteria of the American College of Rheumatology, all SLE patients the 1982 criteria of the American College of Rheumatology, and all MCTD patients met the criteria of Alarcon-Segovia et al. For studies with early arthritis, 54 sera from patients were tested with a commercial CCP2 ELISA autoreactivity were selected. Anti-CCP antibodies were measured by (second generation) enzyme-linked immunosorbent assay (ELISA, Axis Shields Diagnostics) and considered positive at a cut-off value >5 arbitrary units as suggested by the manufacturer.

As shown in FIG. 1, peptides z2 (SEQ ID No. 3), z4 (SEQ ID No. 5), z8 (SEQ ID No. 7) and cz8 (SEQ ID No. 9) show reactivity with serum of a high number of RA patients, whereas the non-citrulline containing counterparts did not show significant reactivity with sera of RA patients. The peptides z2, z4, z8 and cz8 did not show significant reactivity with serum of healthy controls.

As shown in Table 1, peptides of the invention are able to specifically detect serum of RA patients and do not reveal significant cross-reactivity with serum of other RA-negative patients.

TABLE 1

Positive ELISA results are given cumulated for peptides Z1 (SEQ ID No. 14), Z2 (SEQ ID No. 3), Z3 (SEQ ID No. 15), Z4 (SEQ ID No. 5), Z8 (SEQ ID No. 7)

| Diagnosis | n | Positive (n) | Percentage |
| --- | --- | --- | --- |
| Early RA | 54 | 24 | 44% |
| Rheumatoid arthritis | 29 | 22 | 76% |
| Mixed connective tissue disease | 20 | 0 | 0% |
| Primary Sjögren's syndrome | 21 | 0 | 0% |
| Poly/Dermatomyositis | 10 | 0 | 0% |
| Scleroderma | 24 | 0 | 0% |
| SLE | 20 | 0 | 0% |
| Reactive arthritis | 22 | 0 | 0% |
| Osteoarthritis | 26 | 1 | 4% |
| Healthy controls | 24 | 1 | 4% |

In the meantime the total number of individuals with early RA that have been tested has been extended from 54 to 92 while the percentage of positives remained the same.

Example 3

The specific aims of this study were (i) to determine the frequency of Z1 (SEQ ID No. 14), Z2 (SEQ ID No. 3), Z3 (SEQ ID No. 15), Z4 (SEQ ID No. 5), Z8 (SEQ ID No. 7) in early arthritis and positivity in erosive arthritis among patients with very early RA; (ii) to compare the reactivity of Z1 (SEQ ID No. 14), Z2 (SEQ ID No. 3), Z3 (SEQ ID No. 15), Z4 (SEQ ID No. 5), Z8 (SEQ ID No. 7) and CCP2 of patients diagnosed with early RA who did progress to developing erosions to link radiological progression and serological variables, and thus to determine possible prognostic factors for development of erosive disease. Moreover synovial fluid from RA patients were tested.

ELISA tests were performed as described above.

As shown in Table 2, the peptides Z1 (SEQ ID No. 14), Z2 (SEQ ID No. 3), Z3 (SEQ ID No. 15), Z4 (SEQ ID No. 5), Z8 (SEQ ID No. 7) are able to detect early RA with a significant sensitivity and can identify early RA that was not detected by CCP2 ELISA.

TABLE 2

Positive ELISA results are given in % tested sera for each peptide Z1 (SEQ ID No. 14), Z2 (SEQ ID No. 3), Z3 (SEQ ID No. 15), Z4 (SEQ ID No. 5), Z8 (SEQ ID No. 7)

| | | Early RA Serum (n = 54) | Synovial fluid RA patients (74) |
| --- | --- | --- | --- |
| Z1 | GNFMGZGGNFGGGGG | 17% 66% Cit ELISA negative | 28% |
| Z2 | GGGGGNFGZGGNFGG | 17%/ 100% Cit ELISA negative | 57% |
| Z3 | GNFGGZGGYGGGGGG | 8%/ 100% Cit ELISA negative | 17% |
| Z4 | GYGGGGGGSZGSYGG | 25%/ 40% Cit ELISA negative | 57% |
| Z8 | NFGZDGNFGGZGGYG | 32% 90% Cit ELISA negative | 28% |

As summarized in Table 3, peptides Z1 (SEQ ID No. 14), Z2 (SEQ ID No. 3), Z3 (SEQ ID No. 15), Z4 (SEQ ID No. 5), Z8 (SEQ ID No. 7) can be used to distinguish RA with an erosive progression from non-erosive disease with a significant sensitivity and accuracy.

TABLE 3 erosive vs non-erosive disease, ELISA results are given for each peptide given

| | Erosive n = 36 | Non-erosive n = 30 | P (Pearson Chi Square) | PPV % |
| --- | --- | --- | --- | --- |
| RF50 | 21 | 6 | p = 0.002 | 78 |
| Anti-CCP | 22 | 3 | p < 0.001 | 88 |
| Anti-RA33 | 11 | 7 | p = n.s. | 61 |
| cumulated for peptides Z1, Z2, Z3, Z4 and Z8 | 31 | 4 | p < 0.001 | 91 |

The invention claimed is:

1. A peptide or retro or retro-inverso peptide thereof with a length of 5 to 20 amino acid residues for use in diagnosing rheumatoid arthritis, wherein the peptide
   a) comprises at least one citrulline residue, and
   b) exhibits a sequence identity over the whole sequence of the peptide of ≥ 80% compared to SEQ ID No. 2;
   the at least one citrulline residue is located at a position in the sequence of the peptide corresponding to an arginine residue in the sequence of human hnRNP A3 protein.

2. The peptide or retro or retro-inverso peptide according to claim 1, wherein the peptide has the sequence of SEQ ID No. 3, SEQ ID No. 5, SEQ ID No. 7, or SEQ ID No. 9 and the retro peptides thereof has the sequence of SEQ ID No. 10, SEQ ID No. 11, SEQ ID No. 12 or SEQ ID No. 13.

3. The peptide or retro or retro-inverso peptide according to claim 1, wherein the peptide or retro peptide is cyclic.

4. The peptide or retro or retro-inverso peptide according to claim 1, further comprising an effector entity covalently coupled to the peptide via a linker structure.

5. A kit for diagnosing a disease comprising a peptide or retro or retro-inverso peptide according to claim 1.

6. The kit according to claim 5, further comprising at least a second peptide or retro or retro-inverso peptide according to claim 1.

7. A method for in vitro detection of antibodies against a peptide or retro or retro-inverso peptide according to claim 1 comprising the steps of:
   a) providing an isolated body fluid and a peptide or retro or retro-inverso peptide according to claim 1,
   b) bringing in contact the isolated body fluid and the peptide or retro or retro-inverso peptide of step a), and
   c) determining, whether antibodies from the isolated body fluid are bound to the peptide or retro or retro-inverso peptide.

8. The method of claim 7, wherein the body fluid is blood, plasma, serum, synovial fluid, urine, feces, interstital fluid, lymphatic fluid, saliva, sudor, spinal fluid, and/or lacrimal fluid.

9. The method according to claim 7, wherein the isolated body fluid is contacted with at least a second peptide or retro or retro-inverso peptide thereof with a length of 5 to 20 amino acid residues, and the peptide
   a) comprises at least one citrulline residue, and
   b) exhibits a sequence identity over the whole sequence of the peptide of ≥80% compared to SEQ ID No. 2;
   the at least one citrulline residue is located at a position in the sequence of the peptide corresponding to an arginine residue in the sequence of human hnRNP A3 protein.

10. The method according to claim 7, wherein binding of antibodies from the isolated body fluid to the peptide or retro or retro-inverso peptide is determined by radioimmunoassay (RIA), a chemoluminescence immunoassay, an immunoblot assay, or an enzyme immunoassay.

* * * * *